United States Patent [19]

Kuo

[11] Patent Number: 5,334,779
[45] Date of Patent: Aug. 2, 1994

[54] CATALYST COMPOSITIONS AND THE USE THEREOF IN THE HYDROGENATION OF CARBOXYLIC ACID ESTERS

[75] Inventor: Yeong-Jen Kuo, Kingsport, Tenn.

[73] Assignee: Eastman Kodak Company, Rochester, N.Y.

[21] Appl. No.: 69,489

[22] Filed: Jun. 1, 1993

[51] Int. Cl.$^5$ .................. C07C 29/14; C07C 27/04
[52] U.S. Cl. ..................... 568/864; 568/830; 568/831; 568/861; 568/862; 568/876; 568/878; 568/880
[58] Field of Search .............. 568/881, 880, 884, 864, 568/862, 861, 830, 831, 876, 878

[56] References Cited

U.S. PATENT DOCUMENTS

| | | | |
|---|---|---|---|
| 4,113,662 | 9/1978 | Wall | 252/473 |
| 4,149,021 | 4/1979 | Wall | 568/864 |
| 4,918,248 | 4/1990 | Hattori et al. | 568/885 |
| 5,008,235 | 4/1991 | Wegman et al. | 502/342 |
| 5,120,700 | 6/1992 | Matsuda et al. | 502/329 |
| 5,155,086 | 10/1992 | Thakur et al. | 502/342 |
| 5,243,095 | 9/1993 | Roberts et al. | 568/884 |

FOREIGN PATENT DOCUMENTS 2613226  9/1977  Fed. Rep. of Germany ...... 568/884
WO82/03854 11/1982  PCT Int'l Appl.

*Primary Examiner*—Werren B. Lone
*Attorney, Agent, or Firm*—J. Frederick Thomsen

[57] ABSTRACT

Disclosed are catalyst compositions comprised of the oxides of copper, zinc, and a third element selected from the group consisting of aluminum, magnesium, zirconium, and mixtures thereof, and the use of such catalyst compositions in the hydrogenation of carbonyl compounds such as carboxylate esters to obtain the alcohol corresponding to the acid residue of the ester.

10 Claims, No Drawings

CATALYST COMPOSITIONS AND THE USE THEREOF IN THE HYDROGENATION OF CARBOXYLIC ACID ESTERS

This invention pertains to certain novel catalysts comprising oxides of copper, zinc, and a third element selected from the group consisting of aluminum, magnesium, zirconium and mixtures thereof. A second embodiment of the present invention pertains to the use of such catalysts in hydrogenating carbonyl compounds such as carboxylic acid esters to the alcohol which corresponds to the carbonyl compound.

Processes for the hydrogenation of carbonyl compounds in general, and carboxylic acid esters (referred to herein simply as esters) in particular, to alcohols is of significant commercial importance. For example, dimethyl succinate can be hydrogenated to 1,4-butanediol and dimethyl 1,4-cyclohexanedicarboxylate can be hydrogenated to 1,4-cyclohexanedimethanol. Both of these diols are used in substantial quantities in the manufacture of polyesters from which various molded articles and fibers are made. Another example is the manufacture of long chain alcohols by the hydrogenation of natural fats, i.e., glyceryl esters of long chain fatty acids.

Many of the known catalysts which have been used in the hydrogenation of esters to produce alcohols require extremely high pressures, e.g., greater than 272 bars absolute, to achieve commercially-feasible rates of conversion to the desired alcohol. One of the most common catalysts employed in such hydrogenations is copper chromite. See, for example, U.S. Pat. No. 2,091,800. U.S. Pat. No. 5,008,235 discloses the vapor phase hydrogenation of esters in the presence of a catalyst comprising the oxides of copper, aluminum and a third element selected from the group consisting of magnesium, zinc, titanium, zirconium, tin, nickel, cobalt and mixtures thereof. The '235 patent is concerned particularly with the hydrogenation of dialkyl maleates to a mixture of products comprising butanediol, tetrahydrofuran and γ-butyrolactone.

U.S. Pat. No. 5,155,086 discloses the preparation of catalysts comprising the oxides of copper, zinc and aluminum and the use of the catalysts in the processes to hydrogenate aldehydes, ketones, and carboxylic acid esters. This patent provides a detailed description of the state of the art relative to catalysts which contain copper and zinc oxides. U.S. Pat. No. 4,113,622 describes catalysts comprised of the oxides of copper, zinc, and cobalt and the use thereof in the hydrogenation of carboxylic acid esters.

PCT Patent Publication WO 82/03854 reports a process for effecting the hydrogenation of carboxylic acid esters with a catalyst comprising a reduced mixture of copper oxide and zinc oxide. U.S. Pat. No. 4,918,248 discloses a process for the production of alcohols by the reduction of carboxylic acid esters in the presence of a catalyst comprising the oxides of copper, zinc, and titanium. U.S. Pat. No. 5,120,700 discloses the production of higher alcohols from methyl esters using a catalyst comprised of the oxides of copper, iron, aluminum and zinc.

I have discovered that catalyst compositions comprising the oxides of copper, zinc, and a third element selected from the group consisting of aluminum, magnesium, zirconium and mixtures wherein the amount of the third component is not more than 4 weight percent give superior results in the catalytic hydrogenation of carbonyl compounds, especially the hydrogenation of esters to alcohols. The novel catalyst compositions represent a substantial improvement over known ester hydrogenation catalysts of similar composition. Thus, the catalysts of the present invention give improved conversion rates and selectivity in the hydrogenolysis of carboxylate esters at pressures significantly below 272 bars absolute, typically below 170 bars absolute. Moreover, my novel catalyst compositions do not contain toxic metals such as barium or chromium and thus they are safer to manufacture and present fewer environmental problems and occupational hazards in their use and disposal.

One embodiment of the present invention therefore pertains to novel catalyst compositions comprising the oxides of copper, zinc, and a third element (M) selected from the group consisting of aluminum, magnesium, zirconium and mixtures thereof. These mixed oxide compositions contain from 10 to about 80 weight percent copper oxide (calculated as CuO), from 10 to 80 weight percent zinc oxide (calculated as ZnO), and from 0.1 to 4 weight percent of a third component selected from the group consisting of alumina ($Al_2O_3$), magnesia (MgO), zirconia ($ZrO_2$) and mixtures thereof (calculated as the oxide). However, catalytic activity/selectivity for ester hydrogenation, especially when using the preferred conditions of temperature and pressure as described hereinbelow, is unsatisfactory when the copper oxide content of the compositions is below about 15 or above about 80 weight percent, the zinc oxide content is below about 15 or above 80 weight percent, and the third component is above about 4 weight percent. Therefore, the catalyst compositions preferably consist essentially of about 16 to 80 weight percent copper oxide, about 16 to 80 weight percent zinc oxide, and about 0.1 to 4 weight percent of an oxide of the third component M. The preferred compositions contain about 35 to 65 weight percent copper oxide, about 35 to 65 weight percent zinc oxide, and 0.1 to 3 weight percent of the third metal oxide wherein the metal is selected from the group consisting of aluminum, magnesium, zirconium and mixtures thereof.

The essential ingredient of the novel catalyst compositions may be further defined by the formula

$$Cu_aZn_bM_cO_d$$

wherein a, b, c, and d represent atomic ratios and a is about 0.19 to 0.97, b is about 0.25 to 1.01, c is about 0.01 to 0.21, and d is about 1.00 to 1.32 and component M is selected from the group consisting of aluminum, magnesium, zirconium and mixtures thereof. The particularly preferred catalyst compositions are those wherein a is about 0.4 to 0.7, b is about 0.4 to 0.7, c is about 0.01 to 0.08, and d is about 1.1 to 1.3.

My novel catalyst compositions can be used in the form of powders, cylinders, spheres, honeycombs, etc., the physical form being dictated by the type of reactor chosen for and by economic and engineering considerations associated with a particular hydrogenation process.

The catalyst compositions of this invention may be prepared by a variety of methods well known to those skilled in the art. For example, the catalysts can be prepared by precipitating the oxides of copper, zinc, and the third element selected from a group consisting of aluminum, magnesium, zirconium and mixtures thereof by addition of an aqueous alkaline solution to an aqueous solution of water soluble salts of the metal components of the catalyst. Examples of such water soluble salts include the nitrates, acetates, sulfates, chlorides, etc. of copper, zinc, aluminum, and magnesium. Compounds which may be used as the source of the zirconium component include zirconium nitrate, zirconium sulfate, and zirconium chloride, etc. The nitrate salts of each component are preferred for use in the preparation of the catalyst compositions.

The alkaline solution contains at least one alkaline material such as sodium hydroxide, sodium carbonate, sodium bicarbonate, ammonium hydroxide, ammonium carbonate, ammonium bicarbonate, etc., and mixtures thereof. The amount of the alkaline materials in the solution may be varied in a wide range and should be sufficient to precipitate the salts of copper, zinc, and a metal selected from the group consisting of aluminum, magnesium, zirconium and mixtures thereof. A catalyst comprising copper, zinc, and aluminum, for example, can be prepared by first dissolving copper, zinc, and aluminum nitrate in water. A catalyst precipitate is then formed by precipitating copper, zinc, and aluminum by adding ammonium carbonate solution. The precipitated catalyst is dried at about 80° to 120° C. and calcined in air at about 400° to 650° C. for a period of about 30 to 180 min to form a homogeneous mixture of the oxides of copper, zinc, and aluminum.

A second embodiment provided by my invention concerns a hydrogenation process wherein an organic carbonyl compound such as an aliphatic, cycloaliphatic and aromatic carbonyl compound is hydrogenated in the presence of one of the catalyst compositions described hereinabove to convert the carbonyl group to a carbinol or methylol group. Examples of the carbonyl compounds which may be hydrogenated include aliphatic, cycloaliphatic and aromatic aldehydes, esters and ketones containing up to about 40 carbon atoms. Acetophenone, benzophenone, acetone, methyl butyl ketone, benzaldehyde, crotonaldehyde, acetaldehyde and butyraldehyde are typical ketones and aldehydes which may be converted to alcohols according to the present invention. Thus, a preferred embodiment of the novel hydrogenation process provides a process for the preparation of an alcohol by the hydrogenation of an aliphatic, cycloaliphatic or aromatic aldehyde, ester or ketone in the presence of one of the catalyst compositions described hereinabove under hydrogenation conditions of temperature and pressure.

The carbonyl reactant employed in the hydrogenation process preferably is an aliphatic, cycloaliphatic or aromatic ester of an aliphatic or cycloaliphatic mono- or poly-carboxylic acid. The carboxylic acid residue of the ester reactants is not important to our process provided that each oxycarbonyl group hydrogenated is bonded to an aliphatic or cycloaliphatic carbon atom. For example, esters of arylcarboxylic acids such as alkyl benzoates are not included in the ester reactants in our process whereas esters of aralkylcarboxyl acids, such as alkyl phenylacetates are included within the meaning of esters of aliphatic acids. The aliphatic acid residues may be straight- or branched-chain, saturated or unsaturated and unsubstituted or substituted, for example, with a wide variety of substituents such as halogen, hydroxy, alkoxy, amino, substituted amino, acylamido, aryl, cycloalkyl, etc. The main chain of the aliphatic acid residues may contain hetero atoms such as oxygen, sulfur and nitrogen atoms.

Typically, the ester reactants employed in my process may contain up to about 40 carbon atoms. Examples of the carboxylic acid esters include the aliphatic, cycloaliphatic and aromatic esters of acetic, propionic, butyric, valeric, hexanoic, heptanoic, octanoic, nonanoic, decanoic, undecanoic, lauric, tridecanoic, myristic, pentadecanoic, palmitic, heptadecanoic, stearic, oleic, linoleic, linolenic, nonadecanoic, eicosanoic, arachidonic, heneicosanoic, docosanoic, tetracosanoic, octacosanoic, triacontanoic, dotriacontanoic, acrylic, methacrylic, crotonic, 3-butenoic, cyclobutanecarboxylic, 2-norbornanecarboxylic, malonic, succinic, glutamic, maleic, glutaconic, adipic, pimelic, suberic, azelaic, sebacic, 1,2,4-hexanetricarboxylic, 1,2-, 1,3-, and 1,4-cyclohexanedicarboxylic, 2,6- and 2,7-octahydronaphthalenedicarboxylic, 3-1(2-carboxyethyl)thiolbutyric, etc. The alcohol segment of the ester reactants may be the residue of any mono- or polyhydroxy compound such as methanol, ethanol, butanol, 2-butanol, 2-ethylhexanol, 2,2-dimethyl-l,3-propanediol, ethylene glycol, propylene glycol, 1,4-butanediol, 1,6-hexanediol, 1,10-decanediol, cyclohexanol, benzyl alcohol, diethylene glycol, glycerin, trimethylolpropane, phenol, hydroquinone, etc. The hydrogenation process provided by the invention is particularly useful for converting lower, i.e., $C_1$–$C_4$ alkyl esters, especially methyl esters of $C_{10}$–$C_{20}$ carboxylic acids and cyclohexanedicarboxylic acid esters, e.g., dimethyl cyclohexanedicarboxylate.

The amount of catalyst required can be varied substantially depending on a number of factors such as, for example, the composition and physical form of the catalyst and the hydrogenation conditions and mode of operation being used. Furthermore, in certain modes of operation such as trickle bed using a fixed bed of catalyst, the amount of catalyst present relative to the ester reactant is difficult to define with any degree of precision.

The hydrogenation conditions of pressure and temperature also can be varied depending not only on one another but also on the activity of the catalyst, the mode of operation, selectivity considerations and the desired rate of conversion. Esters may be hydrogenated to their corresponding alcohols according to my novel process using temperatures in the range of about 150° to 350° C. and hydrogen pressures in the range of about 34 to 408 bars absolute. However, since hydrogenation rates generally increase with temperature, it is normally desirable to operate in the range of about 200° to 300° C. to maximize both conversion rates and utilization of the commercial hydrogenation facility. While rates and conversions generally also increase with increasing pressure, the energy costs for compression of hydrogen, as well as the increased cost of high-pressure equipment render the use of the lowest pressure practical very advantageous. Thus, a highly attractive feature of my novel process is the use of hydrogen pressures below 204 bars absolute, especially in the range of about 68 to 170 bars absolute, which give good rates of conversion and good selectivities, especially when used in conjunction with a hydrogenation temperature in the range of about 220° to 300° C.

The ester hydrogenation process of this invention may be carried out in the absence or presence of an inert solvent, i.e., a solvent for the ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc.

The hydrogenation process may be carried out as a batch, semi-continuous or continuous process. In batch operation a slurry of the catalyst in the reactant and/or an inert solvent in which the reactant has been dissolved is fed to a pressure vessel equipped with means for agitation. The pressure vessel is then pressurized with hydrogen to a predetermined pressure followed by heating to bring the reaction mixture to the desired temperature. After the hydrogenation is complete the reaction mixture is removed from the pressure vessel, the catalyst is separated by filtration and the product is isolated, for example, in a distillation train.

Continuous operation can utilize a fixed bed using a larger particle size of catalyst, e.g., catalyst pellets. The catalyst bed may be fixed in a tubular or columnar, high pressure reactor and the liquid reactant, dissolved in an inert solvent if necessary or desired, slowly fed continuously above the bed at elevated pressure and temperature and crude product removed from the base of the reactor. Another mode of continuous operation utilizes a slurry of the catalyst in an agitated pressure vessel which is equipped with a filter leg to permit continuous removal of a solution of product in unreacted ester and/or an inert solvent. In this manner a liquid reactant or reactant solution can be continuously fed to and product solution continuously removed from an agitated pressure vessel containing an agitated slurry of the catalyst.

The novel catalyst compositions and the use thereof in the hydrogenation of a typical ester to produce the corresponding alcohol are further illustrated by the following examples.

PREPARATION OF CATALYST COMPOSITIONS

The BET surface area (square meters per g) and the weight percent of each of the oxides present in the catalyst prepared in the following examples are presented in Table I.

EXAMPLE 1

A 2-liter aqueous solution (solution A) containing 93 g of copper nitrate and 119 g of zinc nitrate and a 1-liter aqueous solution (solution B) containing 9.6 g of aluminum nitrate and 115 g of ammonium carbonate are separately prepared. Then solution A is slowly added to solution B with vigorous stirring through a dropping funnel in about 1 hour. The final solution is filtered and the precipitate is washed in distilled water four times. The precipitate collected is then dried at about 100° C. for 120 min and calcined in air at 500° C. for 120 min. The catalyst thus obtained has the formula $Cu_{0.61}Zn_{0.57}Al_{0.04}O_{1.20}$.

COMPARATIVE EXAMPLE 1

A 2-liter aqueous solution (solution A) containing 79.8 g of copper acetate, 87.8 g of zinc acetate, and 52.6 g of aluminum nitrate and a 1-liter aqueous solution (solution B) containing 115 g of ammonium carbonate are separately prepared. Then solution A is slowly added to solution B with vigorous stirring through a dropping funnel in about 1 hour. The final solution is filtered and the precipitate is washed in distilled water four times. The precipitate collected is then dried at about 100° C. for 120 min and calcined in air at 400° C. for 120 min. The catalyst thus obtained has the formula $Cu_{0.47}Zn_{0.52}Al_{0.20}O_{1.28}$.

COMPARATIVE EXAMPLE 2

A 2-liter aqueous solution (solution A) containing 93 g of copper nitrate and 119 g of zinc nitrate, and a 1-liter aqueous solution (solution B) containing 19.7 g of aluminum nitrate and 115 g of ammonium carbonate are separately prepared. Then solution A is slowly added to solution B with vigorous stirring through a dropping funnel in about 1 hour. The final solution is filtered and the precipitate is washed in distilled water four times. The precipitate collected is then dried at about 100° C. for 120 min and calcined in air at 500° C. for 120 min. The catalyst thus obtained has the formula $Cu_{0.52}Zn_{0.63}Al_{0.08}O_{1.28}$.

EXAMPLE 2

Comparative Example 1 is repeated using 45.5 g of magnesium nitrate instead of aluminum nitrate to obtain a catalyst composition containing 3.4 weight percent magnesium oxide. The catalyst has the formula $Cu_{0.49}Zn_{0.69}Mg_{0.09}O_{1.28}$.

EXAMPLE 3

Comparative Example 1 is repeated using 21.5 g of magnesium nitrate instead of aluminum nitrate to obtain a catalyst composition containing 1.4 weight percent magnesium oxide. The catalyst has the formula $Cu_{0.44}Zn_{0.70}Mg_{0.03}O_{1.17}$.

COMPARATIVE EXAMPLE 3

Example 2 is repeated using 99.2 g of magnesium nitrate to obtain a catalyst composition containing 7.7 weight percent magnesium oxide. The catalyst has the formula $Cu_{0.46}Zn_{0.64}Mg_{0.18}O_{1.28}$.

EXAMPLE 4

Comparative Example 1 is repeated using 2.5 g of zirconyl nitrate instead of aluminum nitrate to obtain a catalyst composition containing 1.4 weight percent zirconium oxide. The catalyst has the formula $Cu_{0.69}Zn_{0.42}Zr_{0.01}O_{1.13}$.

EXAMPLE 5

Comparative Example 1 is repeated using 6.4 g of zirconyl acetate instead of aluminum nitrate to obtain a catalyst composition containing 3.3 weight percent zirconium oxide. The catalyst has the formula $Cu_{0.66}Zn_{0.44}Zr_{0.03}O_{1.17}$.

COMPARATIVE EXAMPLE 4

Example 1 is repeated using 15.3 g of zirconyl acetate to obtain a catalyst composition containing 10.1 weight percent zirconium oxide. The catalyst has the formula $Cu_{0.44}Zn_{0.60}Zr_{0.08}O_{1.19}$.

COMPARATIVE EXAMPLE 5

To a 1-liter aqueous solution (solution B) containing 19.7 g of aluminum nitrate and 115 g of ammonium carbonate is added slowly 4.7 g of titanium tetraisoperpoxide. To the resulting mixture is added slowly over a period of about i hour with vigorous stirring through a dropping funnel a 2-liter aqueous solution (solution A) containing 93 g of copper nitrate and 119 g of zinc nitrate. The final solution is filtered and the precipitate is washed in distilled water four times. The precipitate collected is then dried at about 100° C. for 120 min and calcined in air at 500° C. for 120 min. The catalyst thus obtained has the formula $Cu_{0.59}Zn_{0.62}Ti_{0.02}O_{1.25}$.

COMPARATIVE EXAMPLE 6

030 Comparative Example 5 is repeated using 9.4 g of titanium tetraisoperpoxide to obtain a catalyst composition containing 4.3 weight percent titanium oxide. The catalyst has the formula $Cu_{0.55}Zn_{0.58}Ti_{0.05}O_{1.23}$.

TABLE I

| Example | Catalyst | BET | CuO | ZnO | Al₂O₃ | MgO | ZrO₂ | TiO₂ |
|---|---|---|---|---|---|---|---|---|
| 1 | A | 67.3 | 50.1 | 47.8 | 2.1 | — | — | — |
| C-1 | B | 127.5 | 41.4 | 47.4 | 11.2 | — | — | — |
| C-2 | C | 67.2 | 42.9 | 52.7 | 4.4 | — | — | — |
| 2 | D | 52.4 | 39.6 | 57.0 | — | 3.4 | — | — |
| 3 | E | 78.5 | 37.8 | 60.8 | — | 1.4 | — | — |
| C-3 | F | 92.7 | 60.2 | 32.1 | — | 7.7 | — | — |
| 4 | G | 66.3 | 60.6 | 38.0 | — | — | 1.4 | — |
| 5 | H | 66.9 | 57.3 | 39.4 | — | — | 3.3 | — |
| C-4 | I | 83.6 | 37.5 | 52.4 | — | — | 10.1 | — |
| C-5 | J | 40.4 | 47.2 | 51.0 | — | — | — | 1.8 |
| C-6 | K | 44.8 | 46.0 | 50.0 | — | — | — | 4.0 |

HYDROGENATION OF ESTERS

EXAMPLES 6-10 AND COMPARATIVE EXAMPLES 7-12

Each of the catalysts prepared in the preceding examples was evaluated in the catalytic hydrogenation of dimethyl 1,4-cyclohexanedicarboxylate (DMCD) to 1,4-cyclohexanedimethanol (CHDM), a diol widely used in the manufacture of polyesters. Each hydrogenation was conducted in a 1-liter autoclave equipped with a catalyst basket, a stir fin, a thermocouple, a pressure gauge, gas inlet and outlet tubes, a liquid sampling tube and means for heating and cooling the autoclave. In each hydrogenation procedure, DMCD (300 g), methanol (100 g) and the catalyst (15-30 g) were charged to the autoclave. The catalyst was kept inside the basket which was immersed in the reaction mixture. The autoclave was first pressurized to 136 bars absolute with nitrogen, vented and then pressurized to 34 bars absolute with hydrogen at room temperature. Stirring was started and the autoclave was heated to 235° C. at the rate of 1.5° C./minute. The contents of the autoclave were stirred at 235° C. for an additional hour to reduce the catalyst and then the autoclave was pressurized to 163 bars with hydrogen which was the beginning of the 4-hour reaction time employed in each example except Example 6 wherein a reaction period of 2 hours was used. Then the autoclave was cooled and vented carefully to minimize the loss of the contents. The liquid products were analyzed by gas chromatography. The results are summarized in Table II wherein C-7 through C-12 designate the comparative examples, and %MeOH, %DMCD, CMCHM, %CHDM, and %HB are the weight percent of methanol, unreacted dimethyl 1,4-cyclohexanedicarboxylate, 4-(carboxymethyl)cyclohexylmethanol, cyclohexanedimethanol, and high boilers, respectively, in the crude product mixture. The %MeOH includes the methanol used as the process solvent.

TABLE II

| Example | Catalyst | % MeOH | % DMCD | % CMCHM | % CHDM | % HB |
|---|---|---|---|---|---|---|
| 6 | A | 37.6 | 19.7 | 20.5 | 18.1 | 1.2 |
| C-7 | B | 24.8 | 35.8 | 12.3 | 5.3 | 8.2 |
| C-8 | C | 25.7 | 40.4 | 16.4 | 8.0 | 2.0 |
| 7 | D | 33.3 | 8.0 | 16.5 | 32.5 | 3.0 |
| 8 | E | 33.5 | 14.9 | 17.7 | 24.0 | 3.2 |
| C-9 | F | 23.0 | 28.2 | 15.6 | 9.8 | 16.4 |
| 9 | G | 29.4 | 30.7 | 20.8 | 14.5 | 2.6 |
| 10 | H | 30.2 | 15.1 | 20.7 | 24.7 | 2.4 |
| C-10 | I | 28.3 | 30.5 | 16.2 | 112 | 8.8 |
| C-11 | J | 20.9 | 42.4 | 18.4 | 9.5 | 1.9 |
| C-12 | K | 24.0 | 53.9 | 9.2 | 2.8 | 2.2 |

The levels of unreacted DMCD, CHDM, and high boilers (undesired products) in the product provide an indication of catalyst activity/selectivity, i.e., lower levels of unreacted DMCD and higher levels of CHDM in the product indicate higher activities for the catalysts. As shown in Examples 6-10, high conversions of DMCD to CHDM were observed over the catalysts comprising CuO, ZnO, and less than about 4 weight percent Al₂O₃, MgO, and ZrO₂. As the weight percent of Al₂O₃, MgO, and ZrO₂ in the catalyst composition was increased, catalyst activities/selectivities were decreased substantially (Examples C-7 through C-10). Catalysts comprising CuO, ZnO, and less than about 4 weight percent TiO₂ were not as active (Examples C-11 and C-12). Therefore, the results in Table II demonstrate that carboxylic acid esters can be catalytically hydrogenated at good rates and selectivities to their corresponding alcohols using the catalysts described in the present invention.

The invention has been described in detail with particular reference to preferred embodiments thereof, but it will be understood that variations and modifications will be effected within the spirit and scope of the invention.

I claim:

1. A process for hydrogenating a carbonyl compound to the alcohol which corresponds to the carbonyl compound which comprises contacting the carbonyl compound with hydrogen in the presence of a catalyst comprising the oxides of copper, zinc, and a third element selected from the group consisting of aluminum, magnesium, zirconium and mixtures thereof wherein the amount of the oxide of the third component is not more than 4 weight percent under hydrogenation conditions of temperature and pressure.

2. Process according to claim 1 wherein the hydrogen pressure is less than 204 bars absolute and the temperature is about 200° to 300° C.

3. A process for hydrogenating an ester of an aliphatic or cycloaliphatic carboxylic acid to obtain the alcohol corresponding to the acid residue of the ester which comprises contacting the ester with hydrogen in the presence of a catalyst composition comprising from 10 to about 80 weight percent copper oxide (calculated as CuO), from 10 to 80 weight percent zinc oxide (calculated as ZnO), and from 0.1 to 4 weight percent of an oxide of a third component selected from the group consisting of alumina, magnesia, zirconia and mixtures thereof (calculated as the oxide).

4. A process according to claim 3 wherein the catalyst composition consists essentially of about 16 to 80 weight percent copper oxide, about 16 to 80 weight percent zinc oxide, and about 0.1 to 4 weight percent of an oxide of the third component selected from the group consisting of alumina, magnesia, zirconia and mixtures thereof (calculated as the oxide).

5. A process according to claim 3 wherein the catalyst composition consists essentially of about 35 to 65 weight percent copper oxide, about 35 to 65 weight percent zinc oxide, and 0.1 to 3 weight percent of the third metal oxide selected from the group consisting of alumina, magnesia, zirconia and mixtures thereof (calculated as the oxide).

6. A process for hydrogenating an ester of an aliphatic or cycloaliphatic carboxylic acid to obtain the alcohol corresponding to the acid residue of the ester which comprises contacting the ester with hydrogen in the presence of the catalyst composition consisting essentially of about 35 to 65 weight percent copper oxide, about 35 to 65 weight percent zinc oxide, and 0.1 to 3 weight percent of the third metal oxide selected from the group consisting of alumina, magnesia, zirconia and mixtures thereof (calculated as the oxide) at a hydrogen pressure of about 68 to 170 bars absolute and at a temperature of about 220° to 300° C.

7. Process according to claim 6 wherein the ester is dimethyl 1,4-cyclohexanedicarboxylate.

8. Process according to claim 6 wherein the ester is a lower alkyl ester of a $C_{10}$–$C_{20}$ carboxylic acid.

9. Process according to claim 6 wherein the ester is a di-lower alkyl adipate.

10. Process according to claim 6 wherein the ester is a di-lower alkyl maleate.

* * * * *